United States Patent [19]
Bishay

[11] Patent Number: 5,993,219
[45] Date of Patent: Nov. 30, 1999

[54] METHOD AND APPARATUS FOR MODIFYING A RESUSCITATION TRAINING MANNEQUIN

[75] Inventor: Jon M. Bishay, Woodinville, Wash.

[73] Assignee: Heartstream, Inc., Seattle, Wash.

[21] Appl. No.: 08/743,871

[22] Filed: Nov. 5, 1996

[51] Int. Cl.$^6$ ............................ G09B 23/28; A61N 1/18
[52] U.S. Cl. ................. 434/265; 607/5; 600/390
[58] Field of Search .................... 434/262, 265; 607/5; 600/382, 386, 390, 392

[56] References Cited

U.S. PATENT DOCUMENTS

| | | |
|---|---|---|
| 3,453,745 | 7/1969 | Spivack . |
| 4,955,381 | 9/1990 | Way et al. ............................ 600/393 |
| 5,168,875 | 12/1992 | Mitchiner ............................ 600/392 |
| 5,184,620 | 2/1993 | Cudahy et al. ...................... 600/382 |
| 5,191,886 | 3/1993 | Paeth et al. ......................... 600/382 |
| 5,275,572 | 1/1994 | Ungs et al. . |
| 5,518,007 | 5/1996 | Becker ................................ 600/390 |
| 5,617,853 | 4/1997 | Morgan .............................. 600/386 |
| 5,865,741 | 2/1999 | Kelly et al. ......................... 600/386 |

FOREIGN PATENT DOCUMENTS

0499744 A3  8/1992  European Pat. Off. .

*Primary Examiner*—Robert A. Hafer
*Assistant Examiner*—John Edmund Rovnak
*Attorney, Agent, or Firm*—Cecily Anne Snyder

[57] ABSTRACT

This invention relates to an adaptor for use with a a cardiopulmonary resuscitation (CPR) training mannequin. The adaptor has a top layer, a conductor and an adhesive. An additional backing layer may be provided. This invention is also directed to methods of modifying a CPR mannequin through application of an adaptor having communicating conductive areas.

10 Claims, 4 Drawing Sheets

METHOD AND APPARATUS FOR MODIFYING A RESUSCITATION TRAINING MANNEQUIN

BACKGROUND OF THE INVENTION

1. Field of the Invention

This invention relates to a mannequin adaptor for use with a cardiopulmonary resuscitation (CPR) mannequin for training operators in the use of an automatic or semiautomatic external defibrillator (AED). This invention is also directed to methods of modifying a CPR mannequin.

2. Description of the Prior Art

One frequent consequence of heart attacks is the development of cardiac arrest associated with a heart arrhythmia, such as ventricular fibrillation. This abnormal heart rhythm is caused by an abnormal and very fast electrical activity in the heart. During ventricular fibrillation the heart cannot pump blood effectively. Ventricular fibrillation may be treated by applying an electric shock to the patient's heart through the use of a defibrillator. Defibrillation clears the heart of the abnormal electrical activity and allows the heart's natural pacemaker areas to restore normal function. Because blood is no longer pumping effectively during ventricular fibrillation, the chances of surviving a heart attack decrease with time after the attack. Quick response to a heart attack by administering a defibrillating shock as soon as possible after the onset of ventricular fibrillation is therefore often critically important.

Increasing the number of potential defibrillator operators who are trained on the proper use of an external defibrillator increases the likelihood that a trained defibrillator operator is available in an emergency and thus could ultimately reduce defibrillator deployment time. Because of the importance of training defibrillator operators, the prior art has developed different approaches to defibrillator operator training. In one approach, a device generates an electrical signal that simulates either a normal or abnormal heart condition. The signal is delivered to a simulated torso or training mannequin at positions where the sensing electrodes would be properly applied to a patient. The torso also includes terminals for receiving the electrodes that provide the electrical shock. The trainee uses an actual defibrillator on the training mannequin during the training exercise in the same manner as treating a live patient. See, e.g., Spivack U.S. Pat. No. 3,453,745; Ungs et al. U.S. Pat. No. 5,275,572.

In an alternate approach, the trainee does not use an actual defibrillator. Instead, training is conducted on a separate training device which may look like an automatic or semiautomatic defibrillator and simulates the operation of a defibrillator. See, e.g., the Laerdal 911 Trainer. This second type of training device cannot actually be used to deliver a defibrillation shock to a patient. Medical organizations following this defibrillator training approach must therefore have two sets of instruments, one for training and one for actual use. This results in a significant increase in cost.

Yet another approach is the use of a defibrillator having training mode as well as a treatment mode. The training mode simulates the operation of a defibrillator in treatment mode, thus eliminating the need for separate training equipment. See, Cole et al. U.S. Pat. No. 5,611,815, issued Mar. 18, 1997 and Cole, U.S. application Ser. No. 08/648,776 filed May 16, 1996. The disclosures of these applications are incorporated herein by reference. Using a defibrillator with a training mode allows the trainer to use the same defibrillator that is deployed in the field for purposes of training potential users without actually charging and discharging the defibrillator.

It is often useful to train defibrillator users in proper electrode placement. Electrode pads that do make adequate electrical contact with the patient on proper sites on the patient's torso may not deliver effective electrotherapy to the patient. Many defibrillators, when in use to treat a patient, detect whether electrodes pads have been placed on the patient by measuring the impedance between the electrode pads. If the impedance is below a threshold value, then the defibrillator assumes that the electrode pads are on the patient. An impedance value above the threshold value could indicate that one or both of the electrode pads are not connected to the patient. A defibrillator training approach should somehow allow for training on correct electrode placement.

In one training device, a mannequin is provided that has two electrode placement sites provided with Hall-effect sensor arrays. Correct pad placement is determined based on the magnetic field produced by the permanent magnets located in each electrode relative to the sensors. The training defibrillator then prompts the user to relocate the pads as necessary until the correct location has been established. See Ungs et al. EP 0499744 A2. The sensor arrays raise the cost of this training mannequin, however.

The Physio-Control LifePak 100 defibrillator training device was used on a training mannequin with electrode connectors or studs to which metal wire had been attached in an X pattern across the mannequin's electrode connectors. During a training session, the trainee attached the defibrillator training device's electrodes to the mannequin's chest. The defibrillator training device measured the impedance between its electrodes. An impedance below a certain threshold value indicated that the training device's electrodes were properly on the mannequin, i.e., over the metal wire, which completed the circuit between the device's electrodes. The drawback of this approach, however, is that it required the use of a mannequin with protruding metal electrode connectors.

What is needed is a mannequin adaptor and defibrillator training method that permits defibrillator training with all mannequins.

SUMMARY OF THE INVENTION

This invention relates to an adaptor for use with a cardiopulmonary resuscitation (CPR) training mannequin. The adaptor allows the mannequin to be used to train potential users on AED usage. In a preferred embodiment, the adaptor has a top layer, a conductor (such as a conductive layer in the adaptor) capable of communicating with defibrillator electrode pads, and adhesive. Additionally, a removable backing layer may be provided. The conductor may include pad contact areas in electrical communication through, for example, holes in the top layer through which the conductor is exposed. A smooth finish may be provided on the top layer. The smooth finish may be formed from polyvinyl chloride and may be imprinted to enhance training.

This invention also relates to methods of modifying a mannequin for use in defibrillator training, including the steps of aligning electrically communicating conductors of an adaptor strip on defibrillator electrode pad sites on a mannequin and adhering the adaptor strip to the mannequin. The adhering step of the method may include attaching one end of the adaptor to right aspect of the mannequin's clavicle, crossing diagonally across the mannequin's sternum and attaching the second end of the adaptor to the lower left base of the mannequin's ribs below the mannequin's left breast.

The invention is described in further detail below with reference to the drawings.

DESCRIPTION OF THE PREFERRED EMBODIMENTS

Defibrillators fall into three general categories. Manual defibrillators charge and deliver shocks to patients solely in response to user actuation or user request. Automatic defibrillators charge and deliver shocks to patients solely in response to electrocardiogram (ECG) data collected from the patient and analyzed by the defibrillator. Semiautomatic defibrillators analyze patient ECG data and recommend shocks (or recommend that no shock be delivered) but require user actuation to deliver the shock to the patient. This invention may be implemented with automatic or semi-automatic external defibrillators (provided the defibrillator has a training mode that does not deliver an actual shock) or with defibrillator training devices. Examples of suitable devices are described in Cole, et al. U.S. Pat. No. 5,611,815 issued Mar. 18, 1997 and Cole U.S. Ser. No. 08/648,776, described above.

One embodiment of this invention is directed to a mannequin adaptor for use with a defibrillator trainer or an actual defibrillator operating in training mode. A diagram showing an adaptor according to this embodiment is shown in FIG. 1.

Figure 1:
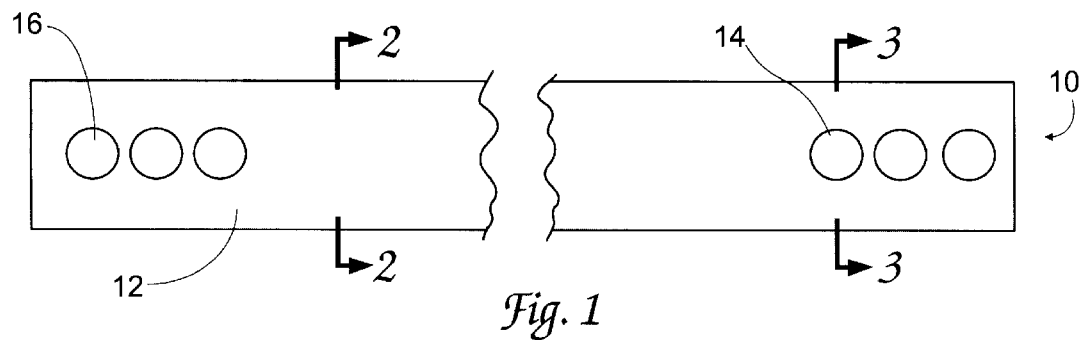
FIG. 1 is a frontal view of a mannequin adaptor.
Figure 2:
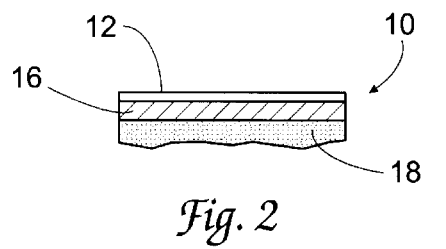
FIG. 2 is a cross-sectional side view of the mannequin adaptor along the lines 2—2 shown in FIG. 1.
Figure 3:
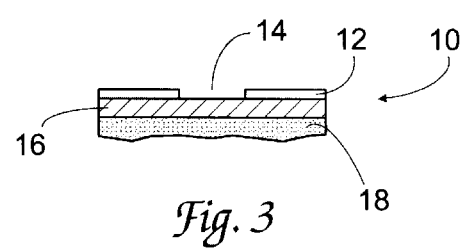
FIG. 3 is a cross-sectional side view of the mannequin adaptor along the lines 3—3 shown in FIG. 1.

As shown in FIGS. 1–3, the adaptor 10 has a top layer 12. An appropriate top layer is any material, such as a polyvinyl chloride film, that has a smooth finish such that the affinity of the hydrogel electrode pads of the defibrillator will be greater for the mannequin than for the adaptor 10. A suitable polyvinyl chloride is a 3 mil film coated on one side with a nonsensitizing acrylic adhesive such as an acrylic copolymer.

Pad contact areas 14 may be provided by, e.g., providing openings in the top layer 12, to allow electrical communication between electrode pads and a conductor 16. These pad contact areas 14 should be situated along the adaptor 10 such that when the adaptor 10 and the electrode pads are applied to the mannequin, the pad contact areas 14 will be located in at least two locations; the first being above the right breast of the mannequin and the second location being the lower left side of the mannequin's ribs. Thus, when the electrode pads are correctly applied the pads will be located on the mannequin in approximately the same anatomical location that the electrode pads would be applied on a patient during actual deployment.

The material comprising the top layer 12 may be colored, multi-colored, imprinted or otherwise marked in such a way as to provide a training aid for placement of the electrode pads 28. A suitable size for the top layer 12 of the adaptor 10 for a standard adult sized mannequin is 1 inch (2.54 cm) wide, 20 inches (50.8 cm) in length and 3 mil in thickness. The pad contact areas 14 may be 0.5 inches (1.27 cm) in diameter and centered along the width of the adaptor 10. In a preferred embodiment, the pad contact areas 14 are located beginning about 1.5 inches (3.81 cm) from each narrow edge of the adaptor 10. Two sets of four 0.5 inch (1.27 cm) diameter pad contact areas, spaced 0.5 inches (1.27 cm) apart beginning at 1.5 inches (3.81 cm) from the narrow edge of the adaptor 10 on either end are effective. Other widths and shapes may be employed without departing from the scope of the invention. A 1.0 inch (2.54 cm) width adaptor allows better conformability to the CPR mannequin upon application.

The conductor 16 is attached to the top layer 12 by any suitable means. In a preferred embodiment, the conductor 16 is attached to the top layer 12 by use of a hypoallergenic, pressure sensitive acrylate adhesive. Other adhesive materials may be used to attach the conductor 16 to the top layer 12 without departing from the scope of the invention.

A suitable conductor 16 is a 1 mil thick layer of Grade A tin. Other suitable conductive materials may be substituted. In the preferred embodiment, the conductor 16 is exposed through the openings in the top layer 12 to form the pad contact areas 14, as shown in FIGS. 1 and 3. The conductor 16 preferably forms a contiguous piece along the length of the adaptor 10 such that the pad contact areas 14 are in electrical communication. As discussed below, when in use, the conductor 16 permits the impedance measurement between the electrode pads by the defibrillator or defibrillator trainer to be below a threshold value.

Also shown in FIGS. 2 and 3 is adhesive 18 is attached to the conductor 14. Additionally, adhesive 18 may be adhered to any portion of the top layer 12 that is not covered by the conductor 16. Any suitable type of repositionable adhesive may be used for this purpose. By "repositionable adhesive" what is meant is an adhesive that is strong enough so that the adaptor will not lift off the mannequin when the electrode pads are removed, but which also allows the adaptor to be removed from the mannequin without damaging the adaptor (thereby allowing it to be reusable) and preferably leaving little or no residue on the mannequin. In a preferred embodiment, a suitable amount of adhesive material should be used so that the adaptor adheres to the mannequin. For example, a layer of 3M 9425 (Minnesota, Mining & Manufacturing Co.) provides the correct amount of adhesiveness. However, other suitable adhesives may be used without departing from the scope of the invention.

Figure 4:
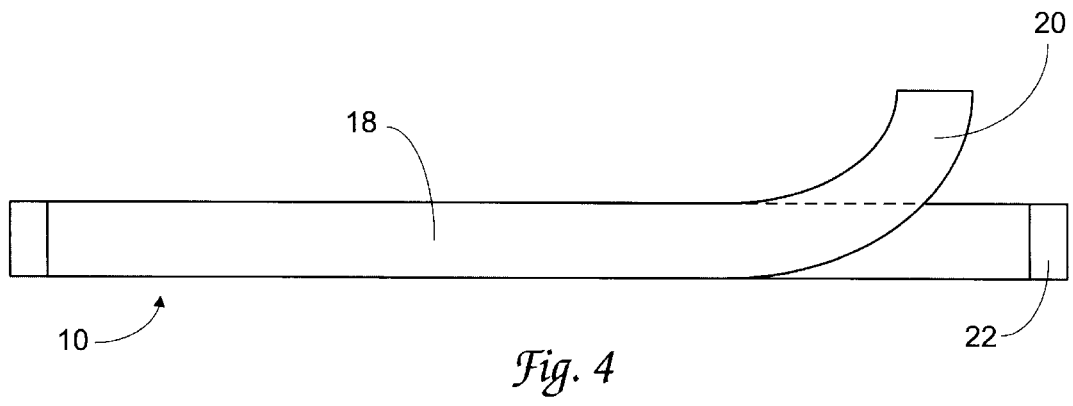
FIG. 4 is a perspective view of the mannequin adaptor.

FIG. 4 shows an optional backing layer 20 being removed from the adaptor 10. The backing layer 20 is typically manufactured from a non-stick liner such as a semi-bleached Kraft release liner (silicone on one side. The backing layer 20 attaches to adhesive 18 and helps to keep the adhesive 18 from losing adhesive properties which may result from exposure to air or other environmental conditions. The backing layer 20 has dimensions at least the same as, or larger than, the adaptor 10.

The backing layer 20 may be situated on the adhesive 18 of the adaptor 10 so that a portion of the adhesive 18 remains covered, thus forming tabs 22. In an alternative embodiment, a tab may be formed at one or both ends of the adaptor by, for example, omitting the adhesive 18 along a selected length of the adaptor 10. Tabs 22 allow the user to manipulate the adaptor 10 in use without directly handling the adhesive 18.

Figure 5:
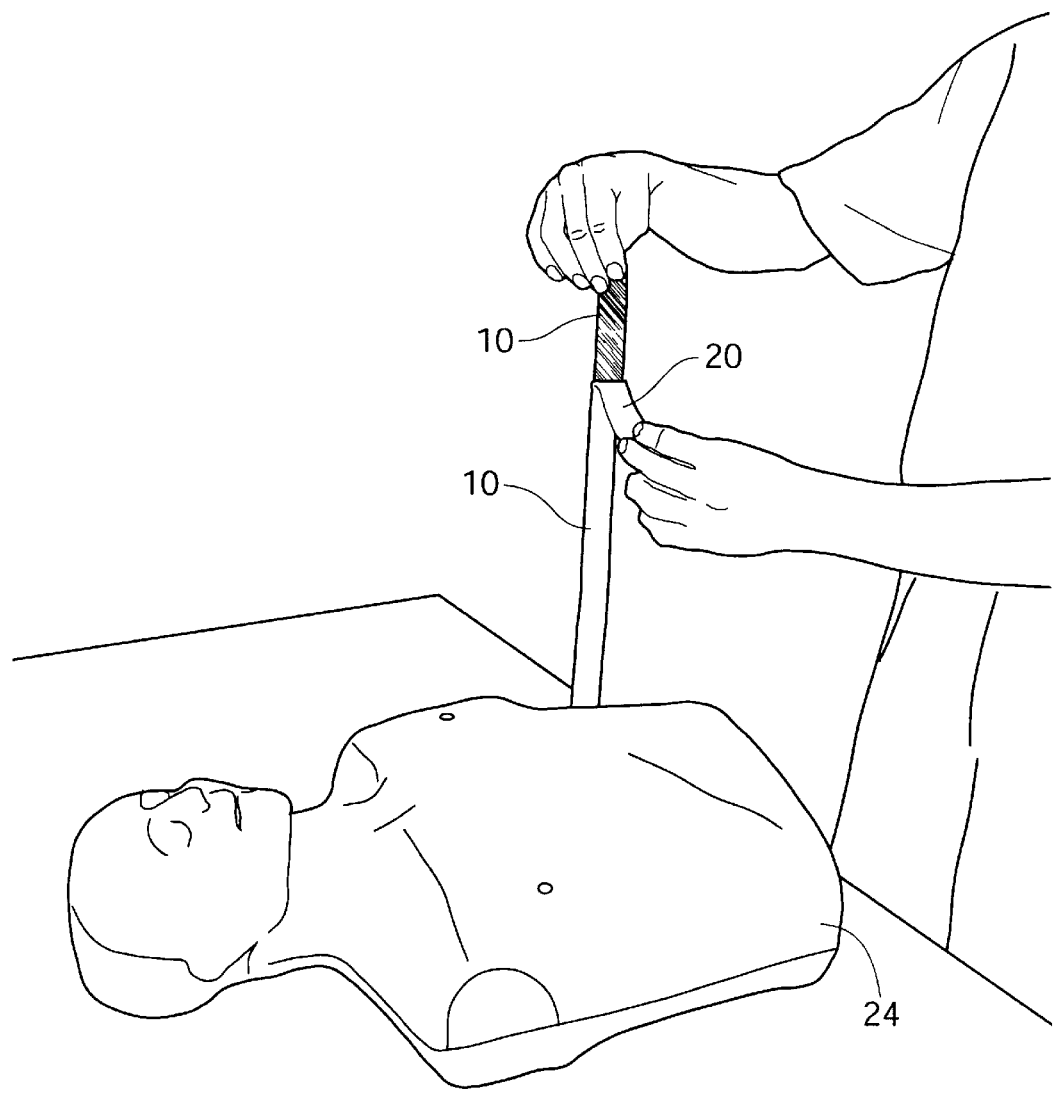
FIGS. 5–7 show the steps of removing the backing layer from the mannequin adaptor, applying the adaptor to the chest of the mannequin, and applying the electrode pads of an AED to the chest of the mannequin such that they make contact with the connector pads of the adaptor.
Figure 6:
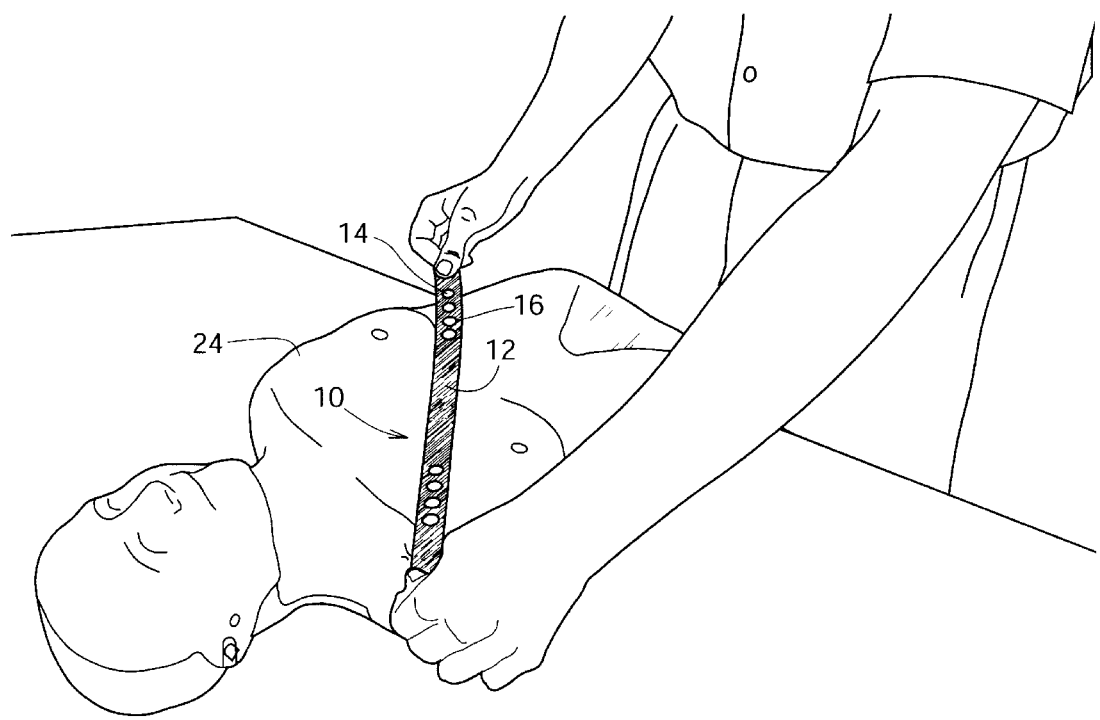
Figure 7:
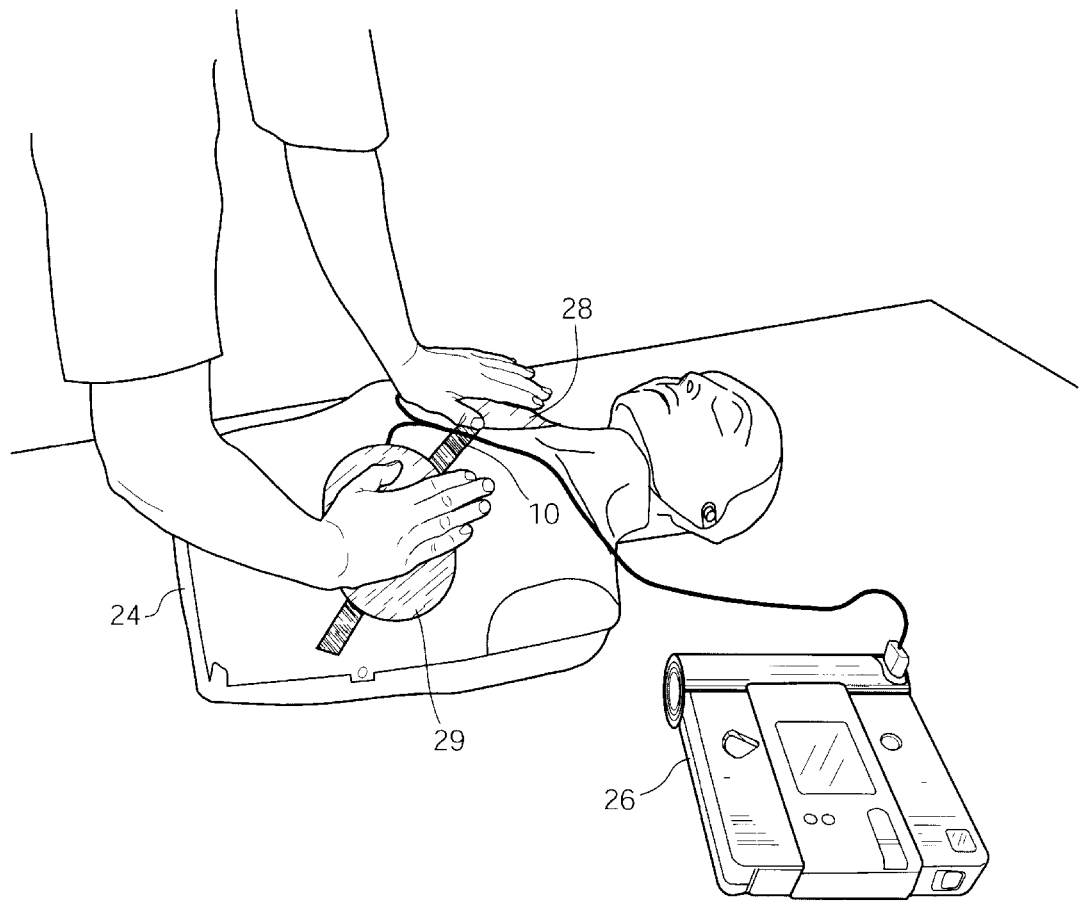

FIGS. 5 through 7 show the method of using the adaptor 10 shown in FIG. 1 during training. FIG. 5 shows the step of removing the backing layer 20 from the adaptor 10. As the backing layer 20 is removed, the adhesive 18 is exposed.

FIG. 6 shows the step of attaching the adaptor 10 to a training mannequin 24. A suitable mannequin would be one used for cardiopulmonary resuscitation (CPR) training having a body manufactured from a material to which the adaptor adhesive will removably adhere. Examples of appropriate mannequins are Resusci® Anne or Little Anne™, by Laerdal (Norway) or Ambu Man, by Ambu (Denmark). Using a mannequin adaptor allows an existing CPR mannequin to be quickly and inexpensively converted to a mannequin suitable for AED training. Because of the flexible design of the adaptor, the mannequin may be used concurrently for CPR training as well as AED training. This is advantageous since typically during an emergency response, an AED would be used in conjunction with CPR. Therefore, training CPR and AED usage on one mannequin allows the user to experience, in the training environment, a sequence of events that could occur during an actual sudden cardiac arrest.

As shown in FIG. 6, the adaptor 10 should be attached to the mannequin 24 across the mannequin's chest so that one end of the adaptor is attached on the right side starting at the right aspect of the mannequin's clavicle and crossing diagonally across the mannequin's sternum toward the lower left base of the mannequin's ribs, below the left breast. Once the adaptor 10 is correctly placed, the pad contact areas 14 (e.g., the exposed portions of the conductor 16) should be approximately positioned on the mannequin's chest at the location where the electrode pads 28 are to be placed during defibrillation. This location anatomically corresponds to the location of a defibrillator's electrode pads during actual use in the field, as shown in FIG. 7.

FIG. 7 shows a defibrillator or defibrillator trainer 26 with the electrode pads 28 placed on the mannequin 24. As explained above, electrode pads 28 should be placed such that one electrode pad is just below the mannequin's right clavicle and the second electrode pad is placed on the mannequin's lower left ribs, below the left breast, such that the electrode pad wraps laterally toward the mid axial line.

Once the adaptor 10 has been affixed to the mannequin 24, and the electrode pads 28 applied to the mannequin chest, the operator may begin operating the defibrillator trainer or the defibrillator in training mode. If the electrode pads 28 are placed over the holes formed at pad contact areas 14 of the adaptor 10, the electrode pads will form a complete circuit through the conductor 16 of the adaptor. The defibrillator or defibrillator trainer 26 may detect that the circuit is complete between the electrode pads 28 by, e.g., measuring impedance between the electrode pads. If the electrode pads are not properly placed so that they make contact with the conductor via the pad contact areas, then the defibrillator or defibrillator trainer will notify the user by, e.g., continuing to request that the user place the electrode pads on the patient's chest.

Other modifications falling within the scope of the invention will be apparent to those skilled in the art. All references cited herein are incorporated by reference in their entirety.

What is claimed:

1. An adapter for use with a cardiopulmonary resuscitation training mannequin comprising:

a top layer having contact areas;

a contiguous conductive layer adhered to one side of the top layer; and adhesive attached to the conductive layer, wherein the conductive layer simulates patient impedance when electrode pads are attached to the exposed contact areas.

2. An adaptor as described in claim 1 additionally comprising:

a removable backing.

3. The adaptor as described in claim 1 wherein the pad contact areas comprise openings in the top layer.

4. An adaptor as described in claim 1 wherein the pad contact areas are located at either end of the adaptor.

5. An adaptor as described in claim 1 wherein the top layer has a smooth finish.

6. An adaptor as described in claim 5 wherein the top layer comprises polyvinyl chloride film.

7. An adaptor as described in claim 1 wherein the top layer is imprinted to enhance training.

8. An adaptor as described in claim 1 wherein the adhesive is a repositionable adhesive.

9. A method of modifying a mannequin for use in defibrillator training comprising the steps of:

aligning electrically communicating conductors of an adapter strip with the defibrillator electrode pad sites of a mannequin; and adhering the adapter strip to the mannequin.

10. The method of claim 9 wherein the step of adhering the adaptor strip to the mannequin further comprises the steps of:

attaching one end of the adaptor to the right aspect of the mannequin's clavicle;

crossing diagonally across the mannequin's sternum; and attaching the second end of the adaptor to the lower left base of the mannequin's ribs below the mannequin's left breast.

* * * * *